US010254220B2

(12) United States Patent
Alkadi et al.

(10) Patent No.: US 10,254,220 B2
(45) Date of Patent: Apr. 9, 2019

(54) METHOD AND SYSTEM FOR REMOTE INSPECTION OF INDUSTRIAL ASSETS

(71) Applicant: General Electric Company, Schenectady, NY (US)

(72) Inventors: Nasr Eldine Alkadi, Oklahoma City, OK (US); Dustin Michael Sharber, Oklahoma City, OK (US); Ashraf Osama El-Messidi, Oklahoma City, OK (US); Radislav Alexandrovich Potyrailo, Niskayuna, NY (US); John Andrew Westerheide, Edmond, OK (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 181 days.

(21) Appl. No.: 15/285,415

(22) Filed: Oct. 4, 2016

(65) Prior Publication Data

US 2018/0095032 A1 Apr. 5, 2018

(51) Int. Cl.
*G01N 21/39* (2006.01)
*G01C 21/20* (2006.01)
(Continued)

(52) U.S. Cl.
CPC .............. *G01N 21/39* (2013.01); *G01C 21/20* (2013.01); *G01S 17/89* (2013.01);
(Continued)

(58) Field of Classification Search
CPC .................. G01N 33/00; G01N 21/39; G01N 2201/06113; H01L 2924/00014;
(Continued)

(56) References Cited

U.S. PATENT DOCUMENTS 4,425,628 A * 1/1984 Bedard .............. H05B 37/0254
710/8
6,766,226 B2 7/2004 Andersen
(Continued)

FOREIGN PATENT DOCUMENTS

CN 104948915 A 1/2015
CN 104279425 A 9/2015

OTHER PUBLICATIONS

International Search Report and Written Opinion issued in connection with corresponding PCT Application No. PCT/US2017/054745 dated Jan. 15, 2018.

(Continued)

*Primary Examiner* — Natalie Huls
*Assistant Examiner* — Mohammed E Keramet-Amircolai
(74) *Attorney, Agent, or Firm* — Christopher R. Carroll; The Small Patent Law Group LLC (57) ABSTRACT

An inspection apparatus includes a communication unit including a first transmitter and a second transmitter. The communication unit is coupled to an on-board computing device including at least one processor coupled to a memory device. The processor is configured to obtain a position of the inspection apparatus, unprocessed image data, and fluid concentration data for at least one fluid. The processor geotags the data with the position of the inspection apparatus and transmits the data to a remote processing device. The geotagged image data is transferred using the first transmitter and the geotagged fluid concentration data is transmitted using the second transmitter.

25 Claims, 4 Drawing Sheets

(51) Int. Cl.
*G01S 17/89* (2006.01)
*G06F 17/30* (2006.01)
*H04Q 9/00* (2006.01)

(52) U.S. Cl.
CPC .. *G06F 17/30241* (2013.01); *G06F 17/30268* (2013.01); *H04Q 9/00* (2013.01); *G01N 2201/06113* (2013.01)

(58) Field of Classification Search
CPC ... H01L 2924/00; G01M 13/04; G01M 99/00; G01C 21/20; G06F 17/30241; G06F 17/30268; G01S 17/89
USPC ............................. 73/865.8, 865.9, 116.08
See application file for complete search history.

(56) References Cited

U.S. PATENT DOCUMENTS

| | | | |
|---|---|---|---|
| 7,027,924 | B2 | 4/2006 | Spoonhower et al. |
| 7,075,653 | B1 | 7/2006 | Rutherford |
| 7,411,196 | B2 | 8/2008 | Kalayeh |
| 8,010,300 | B1 | 8/2011 | Stearns et al. |
| 8,013,303 | B2 | 9/2011 | Ershov et al. |
| 8,284,986 | B2 | 10/2012 | Wolowelsky et al. |
| 8,326,538 | B2 * | 12/2012 | Hobbs .................... E21B 47/12 702/6 |
| 8,345,250 | B1 | 1/2013 | Janosky et al. |
| 9,693,192 | B2 * | 6/2017 | Ishii ...................... H04W 4/023 |
| 9,940,703 | B2 * | 4/2018 | Bozkurt .................... G06T 7/11 |
| 2004/0263852 | A1 | 12/2004 | Degtiarev et al. |
| 2005/0111001 | A1 * | 5/2005 | Potyrailo ........... G01N 21/5907 356/432 |
| 2007/0227250 | A1 * | 10/2007 | Kennedy .............. G01N 29/225 73/641 |
| 2009/0245581 | A1 | 10/2009 | Dey |
| 2010/0305782 | A1 * | 12/2010 | Linden ................. G01C 11/025 701/3 |
| 2011/0079639 | A1 * | 4/2011 | Khan ................. H04N 1/00326 235/375 |
| 2014/0187196 | A1 * | 7/2014 | Okatake ................ H04W 16/18 455/405 |
| 2014/0204197 | A1 * | 7/2014 | Olsson ................. G03B 37/005 348/84 |
| 2014/0260705 | A1 * | 9/2014 | Kimpel, Jr. ........... G01M 99/00 73/865.8 |
| 2014/0340505 | A1 * | 11/2014 | Olsson ............... G01N 21/8803 348/84 |
| 2015/0207385 | A1 * | 7/2015 | Kowalski ................. H02K 5/12 310/55 |
| 2015/0356482 | A1 | 12/2015 | Whipple et al. |
| 2016/0214715 | A1 * | 7/2016 | Meffert ................ B64C 39/024 |
| 2018/0095458 | A1 * | 4/2018 | Sharber ................ G05D 1/0027 |

OTHER PUBLICATIONS

Sadovnychiy et al., "System for Remote Detection of Pipeline Leakage", SPE Latin American and Caribbean Petroleum Engineering Conference, Jun. 20-23, Rio de Janeiro, Brazil, pp. 5, 2005.

B Frish et al., "Standoff and Miniature Chemical Vapor Detectors Based on Tunable Diode Laser Absorption Spectroscopy", IEEE Sensors Journal, vol. 10, Issue: 3, pp. 639-646, Mar. 2010.

Jeff McFadden, "Sensing Methane Using a Tuneable Diode Laser Spectroscopy Method", Offshore Technology Conference, May 5-8, Houston, Texas, pp. 11, 2014.

* cited by examiner

METHOD AND SYSTEM FOR REMOTE INSPECTION OF INDUSTRIAL ASSETS

BACKGROUND

The field of the disclosure relates generally to inspection apparatuses and, more particularly, to a system and method for inspection of industrial assets using inspection apparatuses.

Inspection apparatuses include ground, air, and water-based vehicles that may be autonomous, semi-autonomous, or piloted. Such inspection apparatuses often include onboard navigation systems, such as inertial navigation systems, and satellite navigation systems. Certain known inspection apparatuses further include one or more sensors for capturing data corresponding to the environment in which a given inspection apparatus is operating. For example, some known inspection apparatuses inspect industrial assets, such as oil and gas processing equipment, by capturing sensor data relevant to the operational status of the equipment. Known inspection apparatuses in such applications are generally limited in the amount and type of data they are able to collect due to power limitations. Accordingly, operators are often forced to choose between incomplete data regarding the industrial asset being inspected or the time consuming, expensive, and inefficient course of performing multiple inspection passes of the industrial equipment.

BRIEF DESCRIPTION

In one aspect, an inspection apparatus is provided that includes a communication unit. The communication unit further includes a first transmitter and a second transmitter. The communication unit is coupled to an on-board computing device including at least one processor and a memory device coupled to the at least one processor. The at least one processor is configured to obtain data including a position of the inspection apparatus, unprocessed image data, and fluid concentration data for at least one fluid, and to geotag the unprocessed image data and fluid concentration data. The at least one processor is further configured to transmit the geotagged unprocessed image data using and the geotagged fluid concentration data to a remote processing device. The geotagged unprocessed image data is transmitted using the first transmitter and the geotagged fluid concentration data is transmitted using the second transmitter.

In a further aspect, a method for inspecting an industrial asset using an inspection apparatus including a communication unit including a first transmitter and a second transmitter is provided. The method includes obtaining a position of the inspection apparatus, capturing unprocessed image data, capturing fluid concentration data for at least one fluid, geotagging the fluid concentration data and the unprocessed image data with the position of the inspection apparatus, and transmitting the geotagged unprocessed image data and the geotagged fluid concentration data. The geotagged unprocessed image data is transmitted using the first transmitter and the geotagged fluid concentration data is transmitted using the second transmitter.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "processor" and "computer" and related terms, e.g., "processing device", "on-board computing device", "remote processing device", "remote processing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner.

Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the term "real-time commands" is intended to be representative of instructions formatted to control a control system and related components that are received and then executed in order. These activities occur substantially instantaneously.

As used herein, the term "cloud computing" and related terms, e.g., "cloud computing devices" and "industrial cloud-based platform," refers to a computer architecture allowing for the use of multiple heterogeneous computing devices for data storage, retrieval, and processing. The heterogeneous computing devices may use a common network or a plurality of networks so that some computing devices are in networked communication with one another over a common network but not all computing devices. In other words, a plurality of networks may be used in order to facilitate the communication between and coordination of all computing devices.

As used herein, the term "fluid" is intended to refer to any substance in a liquid, gaseous, or mixed state. Fluids detected and analyzed by asset inspection systems disclosed herein are generally indicative of operational conditions of one or more industrial assets. In oil and gas applications of the disclosed asset inspection system, for example, fluids of interest include, without limitation, methane, water vapor, carbon dioxide, ammonia, hydrogen sulfide, nitrous oxide, non-methane volatile organic compounds, and sulfur dioxide. Nevertheless, the term "fluid" as used herein is not intended to be limited to a specific liquid, gas, or liquid/gas mixture.

The inspection apparatus and associated methods described herein facilitate improved collection of inspection data for industrial assets and, in particular, oil and gas equipment. More specifically, the inspection apparatus and methods described herein facilitate improved remote inspection of oil and gas equipment for purposes of locating and quantifying fluid leaks that may require intervention. To do so, the inspection apparatus described herein includes a range of sensors and equipment configured to collect data, to associate the collected data with a geographic location, and to transmit the data to a remote processing device for processing. Inspection apparatuses in accordance with this disclosure significantly reduce the amount of onboard processing required by the inspection apparatus by directly transmitting unprocessed data, including unprocessed image data, to the remote processing device. To facilitate transmission of the unprocessed data, the inspection apparatus includes at least two transmitters. The first transmitter is used for transmitting the unprocessed image data, while the second transmitter is used to transmit fluid concentration data and other signals from the inspection apparatus. By delegating data processing to the remote processing device, the inspection apparatus facilitates significant reductions in power consumption during an inspection mission. First, the inspection apparatus saves power by not performing on-board processing of the capture data. Second, by not requiring specialized data processing hardware, the overall weight of the inspection apparatus is reduced, thereby reducing the power required to navigate the inspection apparatus between points of interest. For example, by directly transmitting unprocessed image data to the remote processing device, the inspection apparatus does not require on-board image processing hardware, such as a graphics processing unit (GPU). The reduction in power facilitates longer inspection missions by the inspection apparatus and/or the inclusion of additional sensors on the inspection apparatus to provide a more complete inspection of the assets of interest.

Figure 1:
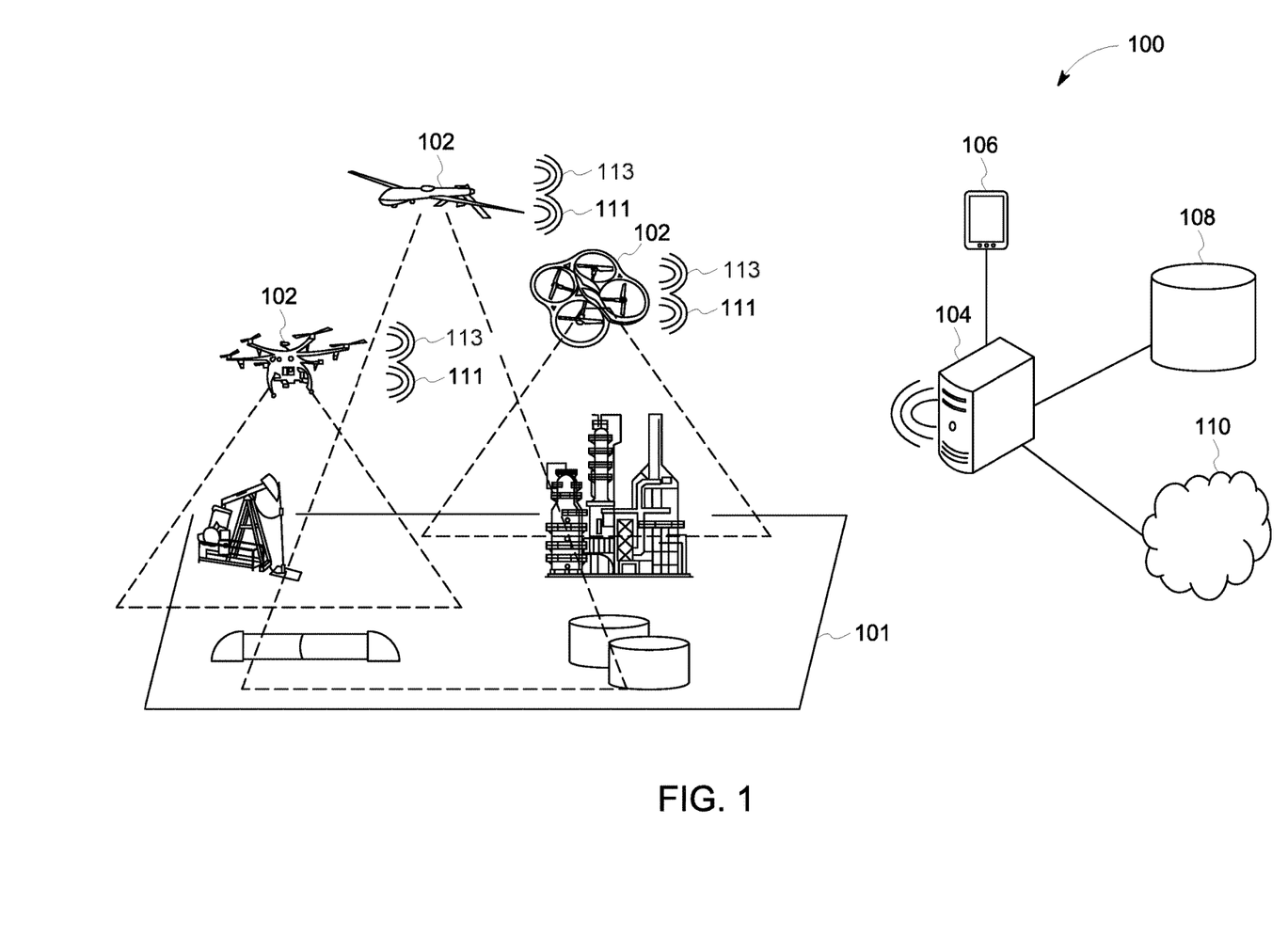
FIG. 1 is a schematic view of an exemplary asset inspection system including one or more inspection apparatuses.

FIG. 1 is a schematic view of an exemplary asset inspection system 100 for inspecting industrial assets in a geographic region 101. In the exemplary embodiment, asset inspection system 100 is configured to inspect oil and gas equipment geographic region 101. Asset inspection system 100 includes one or more inspection apparatuses 102, which, in the exemplary embodiment, are inspection vehicles 102. Each of inspection vehicles 102 is capable of autonomous, semi-autonomous, and fully piloted navigation. Inspection vehicles 102 include, without limitation, aerial, ground-based, and water-based vehicles. Aerial vehicles include, without limitation, fixed wing aircraft, tilt-rotor aircraft, helicopters, multirotor drone aircrafts such as quadcopters, blimps, dirigibles, or other aircrafts. Ground-based inspection vehicles include, without limitation, wheeled vehicles, crawling or walking vehicles, vehicles with tracks, and air-cushioned vehicles (such as hovercrafts). Water-based vehicles include, without limitation, boats and other surface-based vehicles, submarines, and underwater rovers. Each of inspection vehicles 102 is communicatively coupled to a remote processing device 104, using one or more wireless communications standards. In the exemplary embodiment, remote processing device 104 is further communicatively coupled to mobile computing device 106, remote data source 108, and industrial cloud-based platform 110.

During operation, each of inspection vehicles 102 executes route plans configured to navigate inspection vehicles 102 to points of interest in geographic region 101 and to collect data regarding the points of interest. Each of inspection vehicles 102 further includes geolocation units for identifying their respective position. In the exemplary embodiment, each of inspection vehicles 102 includes at least one imaging sensor unit for capturing unprocessed image data and at least one quantitative fluid sensor unit configured to capture fluid concentration data. Accordingly, during execution of the route plan, inspection vehicles 102 navigate to the points of interest specified by the route plans and capture data using the imaging sensor unit and fluid sensor unit. The captured data is then geotagged with the current location of the capturing inspection vehicle and transmitted to remote processing device 104 for additional processing. The captured data is transmitted over multiple channels from each of inspection vehicles 102 to remote processing device 104. For example, each of inspection vehicles 102 transmit geotagged unprocessed image data to remote processing device 104 over a first channel 111 and geotagged fluid concentration data over a second channel 113.

Remote processing device 104 receives and processes data from each of inspection vehicles 102. For example, remote processing device 104 receives geotagged unprocessed image data from inspection vehicles 102 and converts the geotagged unprocessed image data and performs digital image processing on the geotagged unprocessed image data. Digital image processing includes, without limitation, resizing the image, compressing the image, and correcting one or more of color, white balance, brightness, and similar properties of the image. Digital image processing further includes, if necessary, converting the unprocessed image data into a readable and/or displayable file format. Remote processing device 104 also combines the geotagged fluid sensor data with the processed image data to generate a visual representation of the data collected by inspection vehicles 102. In certain embodiments, remote processing device 104 analyzes the geotagged fluid data received from inspection vehicles 102 and determines whether the geotagged fluid data meets predetermined criteria for additional inspection. For example, in certain embodiments, remote processing device 104 determines whether fluid concentration levels indicated by received geotagged fluid concentration data exceeds a predetermined fluid concentration threshold. If so, remote processing device 104 generates a new route plan or modifies an existing route plan to cause one or more of inspection vehicles 102 to reinspect the location associated with the high fluid concentration reading.

Remote processing device 104 is communicatively coupled over one or more networks to other computing devices including mobile computing device 106, remote data source 108, and industrial cloud-based platform 110. Mobile computing device 106 includes, without limitation, a laptop, smartphone, tablet computer, or similar portable device. During operation, an operator uses mobile computing device 106 to view and analyze data provided by inspection vehicles 102 and to issue commands to inspection vehicles 102. More specifically, remote processing device 104 provides mobile computing device 106 with data collected by inspection vehicles in a format displayable on a display (not shown) of mobile computing device 106. The operator then reviews the data collected by inspection vehicles 102 and, if necessary, issues additional commands to inspection vehicles 102 including, without limitation, requests to reinspect a given piece of equipment or point of interest, to inspect a different piece of equipment or point of interest, to end a current route plan, and to begin a different route plan.

Remote data source 108 stores supplemental data accessible by remote processing device 104 for purposes of supplementing the geotagged image and fluid data collected by inspection vehicles 102. Remote data source 108 generally includes one or more storage devices containing one or more databases. Examples of data stored in remote data source 108 include, without limitation, geographic data, meteorological data, previously collected fluid data, and general reference data (e.g., fluid properties and characteristics). By combining the supplemental data with the geotagged fluid and image data captured by inspection vehicles 102, remote processing device 104 generates data visualization with improved sophistication, improved accuracy, and improved utility as compared to data visualizations based only on the geotagged image and fluid data. For example, in one embodiment, remote processing device 104 retrieves supplemental data from remote data source 108 and generates a data visualization including a first layer corresponding to recently collected fluid data and one or more second layers including historical fluid data captured over time, with each layer overlaid on an image of geographic region 101. The data visualization is then transmitted to mobile computing device 106 where a user is able to animate the layers or otherwise turn certain layers of the data visualization on or off to analyze changes in the fluid data over time. Supplemental data from remote data source 108 can also be used to pinpoint the location of fluid leaks. For example, in certain embodiments, remote data source 108 includes weather data, such as wind patterns, that can be used to trace fluid leaks to a point of origin. In yet another example, supplemental data from remote data source 108 includes historical fluid concentration data taken over a period of time and is used to calculate fluid leak rates and total fluid leakage from a given source over the period of time.

Remote processing device 104 is also communicatively coupled to industrial cloud-based platform 110. Industrial cloud-based platform 110 is generally a system of networked computing devices configured to collect and analyze data from the networked computing devices. During operation, remote processing device 104 is configured to provide data collected by inspection vehicles 102 to industrial cloud-based platform 110, which performs various analytics on the provided data. The results of the analytics performed by industrial cloud-based platform 110 are then used to facilitate asset performance management. In certain embodiments, industrial cloud-based platform 110 performs analytics including, without limitation, fluid leak localization, leak rate determination from one or more industrial assets, and total leakage determinations from one or more industrial assets. In certain embodiments, industrial cloud-based platform 110 is communicatively coupled, either directly or indirectly through one or more intermediate computing devices, to one or more pieces of industrial equipment and is able to communicate with and/or control the one or more pieces of industrial equipment in response to the analytics. For example, during one operation, industrial cloud-based platform 110 receives data from remote processing device 104 and, based on an analysis of the received data, determines that a piece of inspected equipment has a fluid leak that exceeds a predetermined leak rate threshold. In response to such a determination, industrial cloud-based platform 110 may take one or more actions including, without limitation, generating and transmitting a report or similar message identifying the leak, issuing a command that modifies one or more control parameters of the equipment, activating or modifying operation of additional equipment associated with the inspected equipment, shutting down the inspected equipment, and issuing an alarm or alert to a control system communicatively coupled to the equipment.

In certain embodiments, at least one of remote processing device 104, and industrial cloud-based platform 110 use fluid concentration data collected by inspection vehicles 102 to analyze leakage from an industrial asset. More specifically, remote processing device 104 and/or industrial cloud-based platform 110 determines leakage based on fluid concentration data collected in a particular location or area over time. Leakage calculations by remote processing device 104 and/or industrial cloud-based platform 110 include determining, without limitation, one or more of a leakage rate, a change in leakage rate, and a total leakage over a period of time. Leakage may be determined based on either mass or volumetric basis. For example, in embodiments in which a leakage rate is calculated, the leakage rate may be expressed in either a volumetric flow rate, such as standard cubic feet per hour, or a mass flow rate, such as pounds per hour.

Figure 2:
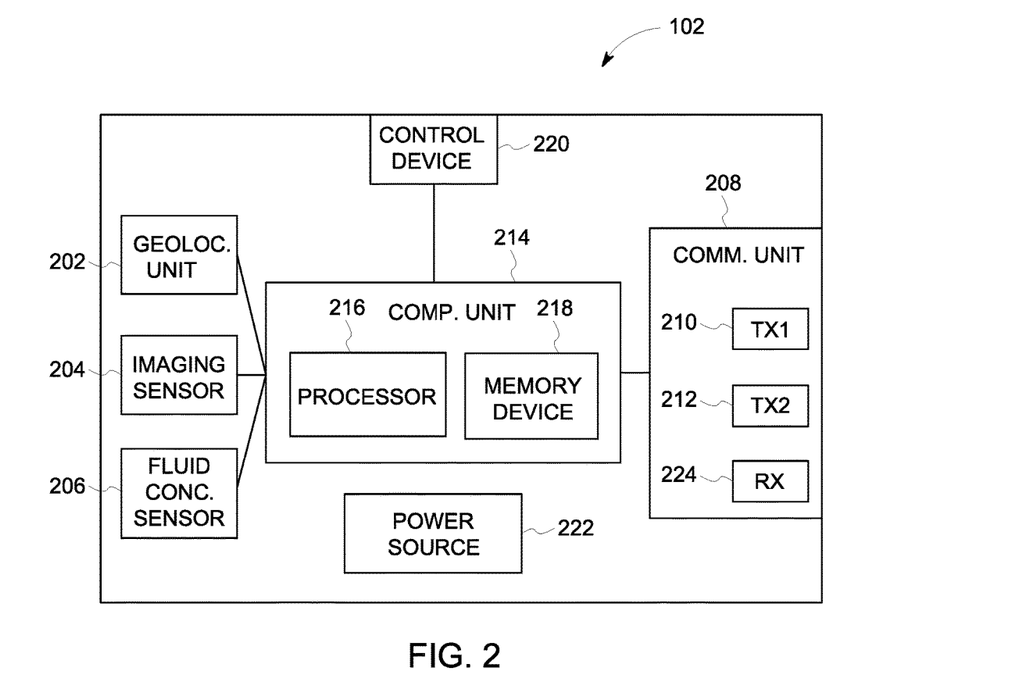
FIG. 2 is an exemplary schematic view of an inspection apparatus for use in the asset inspection system of FIG. 1.

FIG. 2 is a schematic view of an inspection apparatus, namely inspection vehicle 102, of asset inspection system 100 (shown in FIG. 1).

Inspection vehicle 102 includes a geolocation unit 202, an imaging sensor unit 204, a quantitative fluid sensor unit 206, a communication unit 208, an on-board computing device 214, a control device 220, and a power source 222. Communication unit 208 further includes a first transmitter 210, a second transmitter 212, and a receiver 224. On-board computing device 214 further includes at least one processor 216 and a memory device 218 coupled to processor 216.

Processor 216 includes one or more of a microcontroller, a reduced instruction set circuits (RISC), an application-specific integrated circuits (ASICs), a logic circuit, and/or any other circuit or processor that is capable of executing the functions described herein. Processor 216 includes one or more processing units (not shown), such as, without limitation, an integrated circuit (IC), an application specific integrated circuit (ASIC), a microcomputer, a programmable logic controller (PLC), and/or any other programmable circuit. Processor 216 may include multiple processing units (e.g., in a multi-core configuration). Processor 216 executes instructions which perform the functions described herein. The above examples are exemplary only, and thus are not intended to limit in any way the definition and/or meaning of the term "processor."

Memory device 218 includes, without limitation, read-only memory (ROM) and/or random access memory (RAM). Memory device 218 stores executable instructions executable by processor 216 for performing the functions described herein.

Geolocation unit 202 is configured to determine the current position of inspection vehicle 102. More specifically, geolocation unit 202 is configured to generate a set of coordinates locating inspection vehicle 102 in space relative to a frame of reference. The frame of reference may be a global frame of reference or may be a frame of reference relative to another object having a known location. Geolocation unit 202 includes, without limitation, one or more global positioning system (GPS) receivers, laser rangefinders, altimeters, accelerometers, ultrasonic rangefinders, radiolocation systems, and radionavigation systems. Geolocation unit 202 generally produces geolocation data capable of accurately locating inspection vehicle 102 in three-dimensional space. For example, in embodiments in which inspection vehicle 102 includes a global positioning system receiver, geolocation unit 202 produces a set of coordinates including longitude, latitude, and altitude corresponding to the current position of inspection vehicle 102. In certain embodiment, geolocation unit 202 further includes one or more sensors configured to provide the orientation of inspection vehicle 102.

Imaging sensor unit 204 is generally configured to capture visual images of an area being inspected by inspection vehicle 102. Imaging sensor unit 204 includes, without limitation, one or more of a charge-coupled device (CCD) sensor, a complementary metal-oxide semiconductor (CMOS), and a n-type metal-oxide-semiconductor configured to capture (NMOS) sensor configured to capture electromagnetic radiation, such as light, and to convert the electromagnetic radiation into a digital representation of the captured electromagnetic radiation. Imaging sensor unit 204 includes, without limitation, sensors configured to capture one or more of color images, black-and-white images, infrared images (including mid-infrared images), and near infrared images and may include additional components, such as filters, to facilitate capture of such images.

Quantitative fluid sensor unit 206 is generally configured to determine a concentration of one or more fluids. For example, quantitative fluid sensor unit 206 is configured to determine a concentration of, without limitation, one or more of methane, water vapor, carbon dioxide, ammonia, hydrogen sulfide, nitrous oxide, non-methane volatile organic compounds, and sulfur dioxide. In certain embodiments, quantitative fluid sensor unit 206 determines fluid concentration based on one or more optical spectroscopy techniques. In the exemplary embodiment, quantitative fluid sensor unit 206 is a direct spectroscopy sensor unit, such as a tunable diode laser absorption spectroscopy (TDLAS) unit, configured to determine concentration of fluids based on absorption of absorption of a laser produced by the TDLAS unit by the fluid being tested. In other embodiments, quantitative fluid sensor unit 206 includes at least one of an electrochemical fluid sensor, an infrared point sensor, an infrared imaging sensor, a semiconductor fluid sensor, an ultrasonic fluid sensor, a holographic fluid sensor, a direct spectroscopy sensor unit, and an optical filter-based sensor unit. In embodiments including an electrochemical sensor unit, the electrochemical sensor unit further includes a sensing material and a transducer coupled to the sensing material.

The exemplary embodiment of inspection vehicle 102 includes one of each of geolocation unit 202, imaging sensor unit 204, and quantitative fluid sensor unit 206. In alternative embodiments, inspection vehicle 102 includes multiple of at least one of geolocation units, imaging sensor units, and quantitative fluid sensor units. In such embodiments, the additional geolocation units and sensors perform various functions including, without limitation, at least one of providing redundancy, collecting additional data of the same modal type, and collecting additional data of a different modal type. For example, in one embodiment, inspection vehicle 102 includes a first geolocation unit and a second geolocation unit as an emergency backup in case of failure of the first geolocation unit. In another embodiment, inspection vehicle 102 includes a first quantitative fluid sensor configured to measure a fluid concentration using spectroscopic methods and a second quantitative fluid configured to measure a fluid concentration using electrochemical fluid measurement methods.

Communication unit 208 facilitates communication to and from inspection vehicle 102. Communication unit 208 includes a first transmitter 210, a second transmitter 212, and a receiver 224 configured to communicate over at least one of a radio-frequency spectral range, a microwave spectral range, an optical spectral range, and an electromagnetic spectral range. In the exemplary embodiment, communication unit 208 is configured to communicate using first transmitter 210, second transmitter 212, and receiver 224 using a wireless communication standard such as Bluetooth™ or Z-Wave™, through a wireless local area network (WLAN) implemented pursuant to an IEEE (Institute of Electrical and Electronics Engineers) 802.11 standard (i.e., WiFi), and/or through a mobile phone (i.e., cellular) network (e.g., Global System for Mobile communications (GSM), 3G, 4G) or other mobile data network (e.g., Worldwide Interoperability for Microwave Access (WIMAX)), MAVLink, or a wired connection (i.e., one or more conductors for transmitting electrical signals).

Control device 220 produces a controlled force and maintains or changes a position, orientation, or location of inspection vehicle 102. Control device 220 is generally a device configured to change the speed and/or direction of inspection vehicle 102. In embodiments in which inspection vehicle 102 is an aerial vehicle, for example, control device 220 is one of thrust device or a control surface. A thrust device is a device that provides propulsion or thrust to inspection vehicle 102. For example, and without limitation, a thrust device is a motor driven propeller, jet engine, or other source of propulsion. A control surface is a controllable surface or other device that provides a force due to deflection of an air stream passing over the control surface. For example, and without limitation, a control surface is an elevator, rudder, aileron, spoiler, flap, slat, air brake, or trim device. Control device 220 may also be a mechanism configured to change a pitch angle of a propeller or rotor blade or a mechanism configured to change a tilt angle of a rotor blade. In embodiments in which inspection vehicle 102 is a water-based vehicle, control device 220 may include, without limitation, one or more of an engine, a motor, a propeller, a rudder, or any similar device configured to control speed and/or direction of inspection vehicle 102. Similarly, in embodiments in which inspection vehicle 102 is a ground-based vehicles, control device 220 may include, without limitation, one or more of an engine, a motor, a steering mechanism, or any similar device configured to control speed and/or direction of inspection vehicle 102. Control device 220 is communicatively coupled to on-board computing device 214 and configured to respond to real-time commands from processor 216. In certain embodiments, control device 220 is coupled to a control circuit (not shown) configured to convert real-time commands received from processor 216 into movement of an actuator. For example, and without limitation, real-time commands include instructions that, when executed, cause a throttle adjustment, flap adjustment, aileron adjustment, rudder adjustment, or other control surface or thrust device adjustment.

Power source 222 provides power to components of inspection vehicle 102. Power source 222 is, for example, and without limitation, one or more of a battery, solar cell, connection to a power grid, generator, or other source of electrical energy. In certain embodiments, power source 222 includes a wireless charging receiver (not shown) configured to receive electromagnetic energy wirelessly and to use the received electromagnetic energy to charge power source 222. For example, and without limitation, the wireless charging receiver is configured to charge power source 222 by at least one of inductive coupling, resonant inductive coupling, capacitive coupling, magnetodynamic coupling, microwaves, or light transmission to transmit electromagnetic energy. The wireless charging receiver includes one or more antenna devices configured to receive electromagnetic energy. For example, and without limitation, the wireless charging receiver includes wire coils, tuned wire coils, lumped element resonators, electrodes, rotating magnets, parabolic dishes, phased array antennas, lasers, photocells, lenses, and/or other devices for receiving electromagnetic radiation. Power source 222 includes at least one device for storing electrical energy such as a battery, capacitor, fuel cell, and/or other device for storing electrical energy. In alternative embodiments, inspection vehicle 102 is powered by liquid and/or solid fuel. Inspection vehicle 102 includes power source 222 that is a fuel tank or storage device and includes a refueling port (e.g., a probe configured to receive fuel from a drogue or other fuel source). In certain embodiments, power source 222 includes one or more energy harvesting modules configured to capture energy for use by inspection vehicle 102. Energy harvesting modules include, without limitation, modules configured to capture energy from the environment surrounding inspection module 102 and modules configured to capture energy from operation of inspection module 102. For example, energy harvesting modules include, without limitation, solar cells, wind turbines, piezoelectric generators, regenerative braking systems, thermal energy recovery systems, solid oxide fuel cells (SOFC), and kinetic energy recovery systems.

During operation, on-board computing device 214 captures image data using imaging sensor unit 204 and fluid data using quantitative fluid sensor unit 206, and geotags the captured data with location information obtained from geo-location unit 202. On-board computing device 214 then causes the geotagged captured data to be transmitted to remote processing device 104 (shown in FIG. 1) first transmitter 210 and second transmitter 212 of communication unit 208. To avoid the power requirements and added weight of image processing equipment, on-board computing device 214 transmits geotagged image data received from imaging sensor unit 204 using first transmitter 210 in a raw, unprocessed format. Due to the bandwidth required for such transmission, geotagged fluid data is transmitted using a second transmitter 212. By doing so, the extra bandwidth required for transmission of the geotagged unprocessed image data does not interfere with transmission of the geotagged sensor data and/or additional control signals that may be received from remote processing device 104.

During operation, on-board computing device 214 executes a route plan configured to cause inspection vehicle 102 to navigate to one or more points of interest within geographic region 101 (shown in FIG. 1) and to capture sensor data at the one or more points of interest. More specifically, processor 216 is configured to retrieve and execute route plans stored in memory device 218. Each route plan contains one or more route instructions corresponding to at least one of navigation of inspection vehicle 102 or data capture using one or more sensors of inspection vehicle 102. A route plan can include all necessary route instructions for a complete inspection mission or include only a subset of route instructions corresponding to a portion of an inspection mission. Route instructions include, without limitation, general navigation instructions to move inspection vehicle 102 from a first location to a second location; specific instructions regarding control of a specific component of inspection vehicle 102, such as control device 220; and instructions regarding data capture using one of imaging sensor unit 204 and quantitative fluid sensor unit 206. Data capture instructions may include, without limitation, performing a single instance of data acquisition or performing periodic data acquisition. For example, a first set of route instructions causes inspection vehicle 102 to navigate to a first specified location and capture data upon arrival at the first specified location. A second set of route instructions then causes inspection vehicle 102 to navigate from the first specified location to a second specified location and to periodically capture data during transportation between the specified locations. Periodic data capture includes, without limitation, capturing data at a particular frequency (e.g., every 1000 milliseconds (ms)) and capturing data based on a travelled distance (e.g., every 10 meters (m)).

In certain embodiments, route plans and route instructions correspond to pre-programmed logic as opposed to or in addition to a set of predetermined locations. For example, in certain embodiments, route plans include route instructions configured to cause an inspection vehicle to move within a geographic region until the inspection vehicle locates an area having a fluid concentration value that exceeds a predetermined threshold. In response, the route plan causes the inspection vehicle to track the heightened level of fluid concentration to a location at which the fluid concentration is at its highest and to capture data at that location.

During operation, route plans executed by processor 216 are subject to change and/or interruption in favor of executing an alternative route plan. For example, in certain embodiments, processor 216 is configured to analyze captured fluid data to determine whether a fluid concentration at a given location exceeds a predetermined threshold. If so, processor 216 modifies the current route plan or generates a second route plan including reinspection of the location associated with the high fluid concentration. For example, in one embodiment, processor 216 appends one or more route instructions to a currently executing route plan including instructions to return inspection vehicle 102 to the location associated with the high fluid concentration and to perform an additional data capture at that location. Alternatively, processor 216 generates a second route plan and executes the second route plan upon completion of the initial route plan. In a second embodiment, processor 216 temporarily suspends a first route plan, generates a second route plan including route instructions for reinspecting the location associated with the high fluid concentration, and executes the secondary route plan before resuming the second route plan.

In certain embodiments, processor 216 is configured to modify a route plan based on instructions received from communication unit 208 from remote processing device 104 (shown in FIG. 1). Instructions received from remote processing device 104 include instructions generated by remote processing device 104 and instructions generated by at least one of mobile computing device 106 (shown in FIG. 1) and industrial cloud-based platform 110 (shown in FIG. 1). For example, during an inspection operation, inspection vehicle 102 transmits geotagged fluid concentration data to remote processing device 104 which then analyzes the geotagged fluid concentration data, combines the geotagged fluid concentration data with external supplemental data (for example from remote data source 106 (shown in FIG. 1), and determines that at least a portion of the geotagged fluid concentration data or a fluid leak rate corresponding to the geotagged fluid concentration data exceeds a predetermined limit. In response, remote processing device 104 issues a command to inspection vehicle 102 to reinspect the area associated with the portion of the geotagged fluid concentration data. Alternatively, remote processing device 104 receives a similar request or command from one of mobile computing device 106 and industrial cloud-based platform 110. For example, in one embodiment, remote processing device 104 transmits a visualization of the geotagged fluid and image data for display on mobile computing device 106. An operator of mobile computing device 106, upon review of the visualization, selects one or more points of interest that the operator would like to reinspect. The selections are transmitted through remote processing device 104 to inspection vehicle 102 where they are incorporated into a new or existing route plan. In yet another example, remote processing device forwards collected fluid concentration and image data to industrial cloud-based platform 110 for additional analysis and processing. During such processing, industrial cloud-based platform 110 identifies one or more points of interest requiring additional inspection and transmits the points of interest to inspection vehicle 102 through remote processing device 104. Inspection vehicle 102 then incorporates the identified points of interest into a new or existing route plan.

Figure 3:
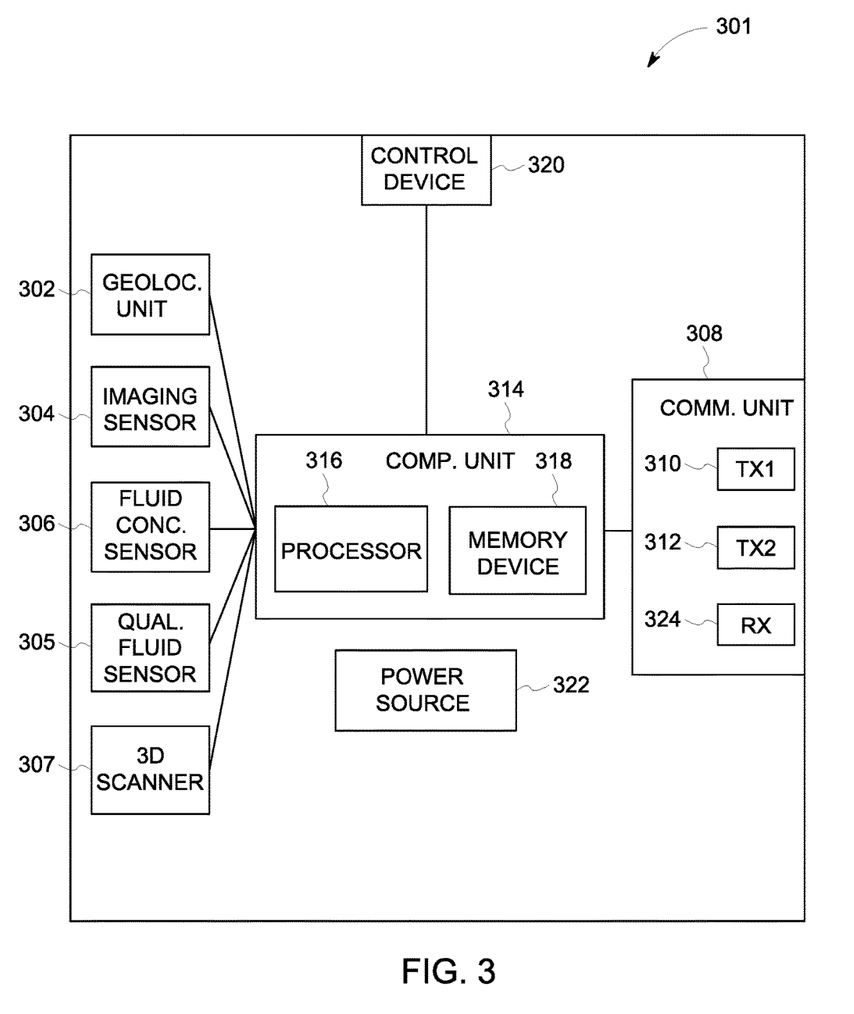
FIG. 3 is a schematic view of an alternative embodiment of an inspection apparatus for use in the asset inspection system of FIG. 1.

FIG. 3 is a schematic view of an alternative embodiment of an inspection apparatus 301, namely inspection vehicle 301, for use in inspection asset inspection system 100 (shown in FIG. 1). Inspection vehicle 301 includes a geolocation unit 302, an imaging sensor unit 304, a qualitative fluid sensor 305, a quantitative fluid sensor unit 306, a three-dimensional scanning unit 307, a communication unit 308, an on-board computing device 314, a control device 320, and a power source 322. Communication unit 308 further includes a first transmitter 310, a second transmitter 312, and a receiver 324. On-board computing device 314 further includes at least on processor 316 and a memory device 318 coupled to processor 316. Except as noted below, each of geolocation unit 302, quantitative fluid sensor unit 306, communication unit 308, on-board computing device 314, control device 320, and power source 322 are configured as described above with respect to their counterparts in inspection vehicle 102.

In contrast to quantitative fluid sensor unit 306, which collects fluid concentration measurements, qualitative fluid sensor unit 305 is configured to capture qualitative fluid data. The term "qualitative fluid data" is used herein to denote fluid data related to the presence of a fluid. In the exemplary embodiment, qualitative fluid sensor unit 305 is an imaging device configured to capture images depicting the size and shape of a fluid plume emanating from a piece of equipment. Such data is particularly useful to characterize plumes of fluids that are otherwise invisible to the naked eye and/or imaging devices configured to capture light in the visible spectrum. In the exemplary embodiment, qualitative fluid sensor unit 305 is an infrared (IR) sensor configured to capture IR image data. IR image data differentiates between the IR characteristics of a fluid plume and the surrounding ambient air, thereby facilitating identification of the overall size and shape of the fluid plume even when the fluid plume is otherwise invisible to the naked eye or conventional imaging sensors. In other embodiments, qualitative fluid sensor unit 305 includes at least one of a mid- and near-infrared sensor.

During operation, processor 316 is configured to operate in conjunction with qualitative fluid sensor unit 305 to capture qualitative fluid data form qualitative fluid sensor unit 305. More specifically, qualitative fluid sensor unit 305 captures qualitative fluid data and transmits the captured qualitative fluid data to on-board computing device 314. Processor 316 then geotags the qualitative fluid data and transmits the geotagged qualitative fluid data to remote processing device 104 (shown in FIG. 1) using second transmitter 312.

Inspection vehicle 301 further includes a three-dimensional scanning unit 307. Three-dimensional scanning unit 307, which in the exemplary embodiment is a light distancing and ranging (LIDAR) unit, generally includes at least one laser unit (not shown) configured to emit a laser, one or more detection units (not shown) configured to detect reflections of the laser, and internal circuitry (not shown) configured to calculate a time-of-travel of the laser and a corresponding distance to the object off of which the laser is reflected. Such distance measurements can then be used to construct a point cloud corresponding to the area scanned by the three-dimensional scanning unit 307.

During operation, processor 316 is configured to operate in conjunction with three-dimensional scanning unit 307 and to receive capture three-dimensional point data. More specifically, three-dimensional scanning unit 307 captures three-dimensional point data and transmits the captured three-dimensional point data to on-board computing device 314. Processor 316 then geotags the three-dimensional point data and transmits the geotagged three-dimensional point data to remote processing device 104 (shown in FIG. 1) using second transmitter 312.

During operation of inspection vehicle 301, processor 316 is configured to control inspection vehicle 301 and to facilitate capture of data using the various sensors mounted thereon. More specifically, processor 316 obtains one or more of a current position using geolocation unit 302, image data from imaging sensor unit 304, qualitative fluid data from qualitative fluid sensor unit 305, quantitative fluid data from quantitative fluid sensor unit 306, and three-dimensional point data from three-dimensional scanning unit 307, to geotag each piece of data, and to transmit the geotagged data to remote processing device 104 (shown in FIG. 1) for additional processing. More specifically, inspection vehicle 301 includes a communication unit 308 having a first transmitter 310 for exclusively transmitting geotagged unprocessed image data obtained from imaging sensor unit 304 and a second transmitter 312 for transmitting the remaining geotagged data. In certain embodiments, communication unit 308 includes one or more additional transmitters such that the remaining geotagged data is divided across multiple channels during transmission.

In certain embodiments, processor 316 merges the geotagged quantitative fluid data with one or both of the geotagged qualitative fluid data and the geotagged three-dimensional point data to generate a fluid data mesh prior to transmission by inspection vehicle 301. More specifically, processor 316 associates the geotagged quantitative fluid data obtained from quantitative fluid sensor unit 306 with one or both of the geotagged qualitative fluid data generated by qualitative fluid sensor unit 305 and the geotagged three-dimensional point data generated by three-dimensional scanning unit 307. In one embodiment, for example, processor 316 associates the geotagged quantitative fluid data with the geotagged qualitative image data to generate a two-dimensional array wherein each element of the array includes both qualitative and quantitative fluid data, the two-dimensional array representing a portion of geographic region 101 (shown in FIG. 1).

Similarly, in alternative embodiments, the geotagged quantitative fluid data is associated with the geotagged three-dimensional point data to generate a three-dimensional fluid data mesh. In such embodiments, the fluid data mesh comprises a three-dimensional array wherein each array entry corresponds to a point in space of geographic region 101 and includes both quantitative fluid data and an indication of whether three-dimensional scanning unit 307 identified a point at that location. Accordingly, the three-dimensional data map may be used to define a topographic map including a fluid concentration reading at each point.

In certain embodiments, the geotagged quantitative fluid data may be correlated with each of the geotagged qualitative fluid data and the geotagged three-dimensional point data based on the geotags assigned to each piece of data. More specifically, the geotagged quantitative fluid data, geotagged qualitative fluid data, and geotagged three-dimensional point data are correlated and combined based, at least in part, on the geolocation represented by the geotag assigned to each piece of data. In alternative embodiments, association of the geotagged quantitative fluid data and each of the geotagged qualitative fluid data and the geotagged three-dimensional point data is further based on additional data including, without limitation, position and orientation on inspection vehicle 301 of each of the qualitative fluid sensor unit 305, the quantitative fluid sensor unit 306, and the three-dimensional scanning unit 307 during data capture on inspection vehicle 301; position and orientation relative to each other of the qualitative fluid sensor unit 305, the quantitative fluid sensor unit 306, and the three-dimensional scanning unit 307 during data capture; and direction and speed of travel of inspection vehicle 301 during data capture.

Figure 4:
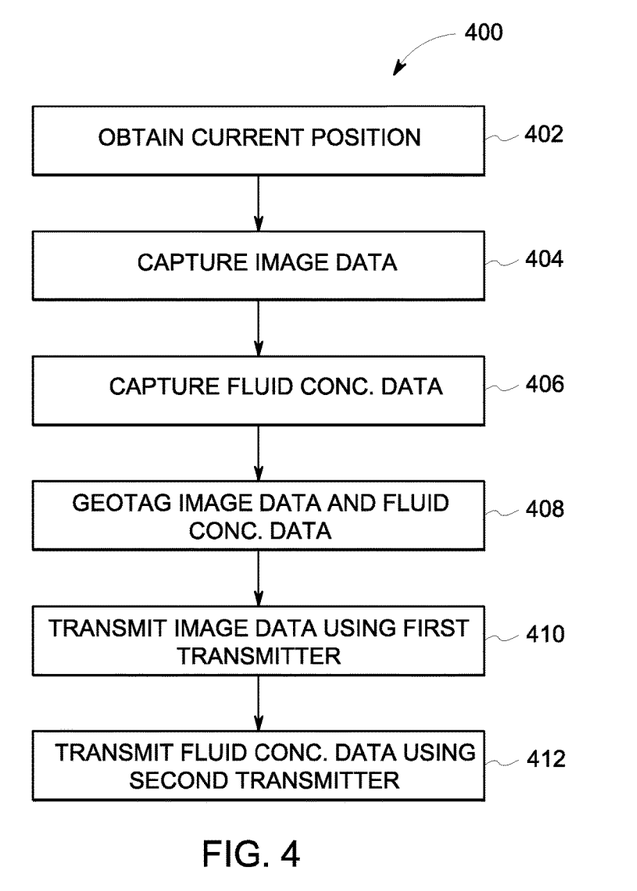
FIG. 4 is a flow chart of an exemplary method of inspecting an industrial asset using the inspection apparatus of FIG. 2.

FIG. 4 is a flow chart of an exemplary method 400 of inspecting an industrial asset data using an inspection apparatus, namely inspection vehicle 102 (shown in FIGS. 1 and 2). As noted above, inspection vehicle 102 generally includes a geolocation unit 202, an imaging sensor unit 204, a quantitative fluid sensor unit 206, and a communication unit 208, which further includes a first transmitter 210 and a second transmitter 212 (all shown in FIG. 2).

Method 400 includes, at step 402, obtaining a current position of inspection vehicle 102 from geolocation unit 202. For example, in certain embodiments, inspection vehicle 102 includes a processor, such as processor 216, (shown in FIG. 2) communicatively coupled to geolocation unit 202. During operation, processor 216 issues one or more requests to geolocation unit 202 for the current position of inspection vehicle 102. In certain embodiments, geolocation unit 202 automatically periodically determines the current position of inspection vehicle 102 and transmits the most recently determined position to processor 216 in response to receiving a request from processor 216. Alternatively, geolocation unit 202 determines the current location dynamically upon receipt of a request from processor 216.

At steps 404 and 406, image and fluid concentration data are captured by inspection vehicle 102. More specifically, processor 216 issues instructions or requests to each of imaging sensor unit 204 and quantitative fluid sensor unit 206. In response, imaging sensor unit 204 and quantitative fluid sensor unit 206 capture image data and fluid concentration data, respectively.

At step 408, each of the image data and the fluid concentration data are geotagged with the position data provided by geolocation unit 202. Geotagging of the collected data can be performed in various ways including, without limitation, generating a data structure containing the captured data and the position of inspection vehicle 102; populating a metadata field of a data file containing the collected data with the current position of inspection vehicle 102; and constructing a message containing the collected data, wherein the message includes a message header including the current position of inspection vehicle 102. Inspection vehicle 102 transmits the geotagged image data and the geotagged quantitative fluid data at steps 410 and 412, respectively. More specifically, the geotagged image data is transmitted using first transmitter 210 and the geotagged fluid concentration data is transmitted using second transmitter 212.

The above-described apparatus and method provide for enhanced inspection of industrial assets using inspection vehicles. The method and systems described herein allow for enhanced inspection of an industrial asset by the inspection vehicle as the inspection vehicle is configured to include and operate using multi-modal sensors. More specifically, the inspection vehicle performs limited on-board processing, facilitating removal of unnecessary data processing systems or replacement of such data processing systems with additional sensors. Limited on-board processing also significantly reduces the amount of power consumed by data processing, thereby allowing for longer inspection missions and a greater quantity of sensor data collected on a given inspection mission.

An exemplary technical effect of the apparatus and methods herein includes at least one of: (a) improving data collection by facilitating replacement of data processing equipment with additional sensor units; (b) improving inspection time by reducing inspection vehicle weight; (c) improving inspection time by reducing power consumption required for on-board data processing; (d) improving efficiency of inspection missions by quickly and accurately providing sensor data to one or more of a remote processing device, an operator remote processing device, and an industrial cloud-based platform configured to modify aspects of the inspection mission in response to collected data; and (e) facilitating data collection that more accurately reflects operational conditions of an industrial asset.

Exemplary embodiments of method and systems for inspecting an industrial asset using an inspection vehicle are described above in detail. The method and systems described herein are not limited to the specific embodiments described herein, but rather, components of systems or steps of the methods may be utilized independently and separately from other components or steps described herein. For example, the apparatus and methods disclosed herein may be implemented in applications outside of the oil and fluid industry for purposes of monitoring operating conditions of other pieces of industrial equipment. Additionally, the methods may also be used with other components of devices, and are not limited to practice with only the components as described herein. Rather, the exemplary embodiments may be implemented and utilized in connection with many other unmanned vehicles and asset inspection systems.

Although specific features of various embodiments may be shown in some drawings and not in others, this is for convenience only. In accordance with the principles of the systems and methods described herein, any feature of a drawing may be referenced or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An inspection apparatus comprising:
   a communication unit comprising:
      a first transmitter; and
      a second transmitter; and
   an on-board computing device coupled to said communication unit, said on-board computing device comprising at least one processor and a memory device coupled to said at least one processor, said at least one processor configured to:
      obtain a current position of said inspection apparatus;
      capture unprocessed image data;
      capture fluid concentration data for at least one fluid;
      geotag the fluid concentration data and the unprocessed image data with the position of said inspection apparatus;
      transmit the geotagged unprocessed image data to a remote processing device using said first transmitter, wherein the remote processing device is located remotely from said inspection apparatus; and
      transmit the geotagged fluid concentration data to the remote processing device using said second transmitter.

2. The inspection apparatus in accordance with claim 1 further comprising a geolocation unit, wherein said on-board computing device is coupled to said geolocation unit and said at least one processor is further configured to obtain the current position of said inspection apparatus from said geolocation unit.

3. The inspection apparatus in accordance with claim 1 further comprising an imaging sensor unit, wherein said on-board computing device is coupled to said imaging sensor unit and said at least one processor is further configured to capture the unprocessed image data from said imaging sensor unit.

4. The inspection apparatus in accordance with claim 1 further comprising a quantitative fluid sensor unit, wherein said on-board computing device is coupled to said quantitative fluid sensor unit and said at least one processor is further configured to capture said fluid concentration data for the at least one fluid from said quantitative fluid sensor unit.

5. The inspection apparatus in accordance with claim 4, wherein said quantitative fluid sensor unit is at least one of a direct spectroscopy sensor unit, an optical filter-based sensor unit, and a chemical sensor unit, said chemical sensor unit comprising a sensing material and a transducer coupled to said sensing material.

6. The inspection apparatus in accordance with claim 4, wherein said quantitative fluid sensor unit is a direct spectroscopy sensor, and said direct spectroscopy sensor is a tunable diode laser absorption spectroscopy (TDLAS) unit.

7. The inspection apparatus in accordance with claim 1 further comprising a qualitative fluid sensor unit configured to generate qualitative fluid data, wherein said on-board computing device is coupled to said qualitative fluid sensor unit, and wherein said at least one processor is further configured to capture qualitative fluid data using said qualitative fluid sensor unit, geotag the qualitative fluid data with the current position of said inspection apparatus, and transmit the geotagged qualitative fluid data to the remote processing device using said second transmitter.

8. The inspection apparatus in accordance with claim 7, wherein said at least one processor is further configured to generate a fluid data mesh associating the geotagged fluid concentration data and the geotagged qualitative fluid data, and wherein said at least one processor is further configured to transmit the geotagged fluid concentration data and the qualitative fluid data by transmitting the fluid data mesh using said second transmitter.

9. The inspection apparatus in accordance with claim 7, wherein said qualitative fluid sensor unit is at least one of an infrared sensing unit, a mid-infrared sensing unit, and a near infrared sensing unit.

10. The inspection apparatus in accordance with claim 1, wherein said at least one processor is further configured to capture three-dimensional topographic data, geotag the three-dimensional topographic data, and transmit the geotagged three-dimensional topographic data to the remote processing device using the second transmitter.

11. The inspection apparatus in accordance with claim 10 further comprising a three-dimensional scanning unit configured to generate the three-dimensional topographic data, wherein said on-board computing device is coupled to said three-dimensional scanning unit, and wherein said at least one processor is further configured to capture the three-dimensional topographic data using said three-dimensional scanning unit.

12. The inspection apparatus in accordance with claim 11, wherein said three-dimensional scanning unit is a light distancing and ranging (LIDAR) unit.

13. The inspection apparatus in accordance with claim 10, wherein said at least one processor is further configured to generate a three-dimensional fluid data mesh associating the geotagged fluid concentration data and the geotagged three-dimensional topographic data, and wherein said at least one processor is configured to transmit the geotagged fluid concentration data and the geotagged three-dimensional topographic data by transmitting the three-dimensional fluid data mesh.

14. The inspection apparatus in accordance with claim 1 further comprising, a control device configured to control a position of said inspection apparatus, wherein said on-board computing device is coupled to said control system, wherein said memory device includes a first route plan including one or more first route instructions, and wherein said at least one processor is further configured to execute the route plan by issuing each of the one or more first route instructions to said control device.

15. The inspection apparatus in accordance with claim 14, wherein said at least one processor is further configured to:
determine that the geotagged fluid concentration data exceeds a predetermined fluid concentration limit;
modify the route plan to include one or more second route instructions configured to cause said inspection apparatus to return to the position of said inspection apparatus and to recapture at least one of additional unprocessed image data and additional fluid concentration data; and
execute the modified route plan by issuing each of the one or more second route instructions to said control device.

16. The inspection apparatus in accordance with claim 14, wherein said communication unit further comprises a receiver, wherein said at least one processor is further configured to:

receive, by said receiver, from the remote processing device, and in response to transmitting at least one of the geotagged unprocessed image data and the geotagged fluid concentration data, a second route plan including one or more second route instructions; and
execute the second route plan by issuing each of the one or more second route instructions to said control device.

17. The inspection apparatus in accordance with claim 1, wherein said first transmitter and said second transmitter are configured to transmit the geotagged unprocessed image data and the geotagged fluid concentration data, respectively, using transmission in at least one of a radio-frequency spectral range, a microwave spectral range, an optical spectral range, and an electromagnetic spectral range.

18. The inspection apparatus in accordance with claim 1, wherein said first transmitter and said second transmitter are configured to transmit the geotagged unprocessed image data and the geotagged fluid concentration data, respectively, using at least one of Wi-Fi, WiMAX, Bluetooth, 3G, 4G, and MAVLink.

19. A method of inspecting industrial assets using an inspection apparatus including a communication unit including a first transmitter and a second transmitter, said method comprising:
obtaining a position of the inspection apparatus;
capturing unprocessed image data;
capturing fluid concentration data for at least one fluid;
geotagging the fluid concentration data and the unprocessed image data with the position of the inspection apparatus;
transmitting the geotagged unprocessed image data to a remote processing device using the first transmitter; and
transmitting the geotagged fluid concentration data to the remote processing device using the second transmitter.

20. The method in accordance with claim 19 further comprising:
capturing qualitative fluid data;
geotagging the qualitative fluid data with the position of the inspection apparatus; and
transmitting the qualitative fluid data using the second transmitter.

21. The method in accordance with claim 19 further comprising generating a fluid data mesh by associating the geotagged fluid concentration data and the geotagged qualitative fluid data, wherein the geotagged fluid concentration data and the geotagged qualitative fluid data are transmitted by transmitting the fluid data mesh.

22. The method in accordance with claim 19 further comprising:
capturing three-dimensional topographic data;
geotagging the three-dimensional topographic data; and
transmitting the geotagged three-dimensional topographic data to the remote processing device using the second transmitter.

23. The method in accordance with claim 22 further comprising generating a three-dimensional fluid data mesh by associating the geotagged fluid concentration data and the geotagged three-dimensional topographic data, wherein the geotagged fluid concentration data and the geotagged three-dimensional topographic data are transmitted by transmitting the three-dimensional fluid data mesh.

24. The method in accordance with claim 19 further comprising:
determining that the geotagged fluid concentration data exceeds a predetermined fluid concentration limit;

generating a route plan including one or more route instructions configured to cause the inspection apparatus to return the position of the inspection apparatus and to capture at least one of additional unprocessed image data and additional fluid concentration data; and executing the route plan.

25. The method of claim 19 further comprising:

receiving, from the remote processing device, in response to transmitting the unprocessed image data and the fluid concentration data, a route plan including one or more route instructions; and executing the route plan.

\* \* \* \* \*